United States Patent
Shepherd, Jr.

(10) Patent No.: US 6,290,939 B1
(45) Date of Patent: *Sep. 18, 2001

(54) DEDUSTED BLEACH COMPOSITION, PROCESS FOR PRODUCING THE COMPOSITION AND USES THEREOF

(75) Inventor: Walter B. Shepherd, Jr., Warwick, NY (US)

(73) Assignee: CCP, Incorporated, West Patterson, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/009,482

(22) Filed: Jan. 20, 1998

(51) Int. Cl.[7] ............... A61K 7/06; A61K 7/135
(52) U.S. Cl. ............ 424/62; 424/70.1; 424/70.11; 424/70.22
(58) Field of Search ................... 424/62, 70.11, 424/70.22, 70.1

(56) References Cited

U.S. PATENT DOCUMENTS 5,612,022  3/1997  Tricaud et al. ............... 424/62
5,622,691  4/1997  Tricaud et al. ............... 424/62

FOREIGN PATENT DOCUMENTS

| 0560088A1 | 9/1993 | (EP) . |
| 0574696A2 | 12/1993 | (EP) . |
| 0583767A2 | 2/1994 | (EP) . |
| 0630643A1 | 12/1994 | (EP) . |
| 2703588 | 10/1994 | (FR) . |

Primary Examiner—Thurman K. Page
Assistant Examiner—S. Howard
(74) Attorney, Agent, or Firm—Cooper & Dunham LLP; Robert D. Katz

(57) ABSTRACT

The present invention provides for a composition for bleaching hair consisting essentially of: (a) an oxidizing agent selected from any peroxygen compound, and (b) a linear hydroxy terminated polyoxypropylene oligomer which comprises from 0.5% to 15% by weight relative to the total weight of the composition. The linear hydroxy terminated polyoxypropylene oligomer may comprise an oil like material having a pour point less than 0 degress Fahrenheit. The present invention also provides for a process for the preparation of a composition for bleaching hair which comprises mixing a linear hyroxy terminated polyoxypropylene oligomer into the composition for bleaching hair, spraying the mixture at room temperature to apply a uniform coating of the oligomer on particles of the composition, thereby causing the particles to agglomerate so as to render the composition essentially dust free during handling.

18 Claims, No Drawings

DEDUSTED BLEACH COMPOSITION, PROCESS FOR PRODUCING THE COMPOSITION AND USES THEREOF

FIELD OF THE INVENTION

This invention relates to improved hair bleaches, and more particularly to dust free hair bleaches and methods of their manufacture.

BACKGROUND OF THE INVENTION

Hair bleach routinely originates as a powdery mixture of ingredients which are then transformed into a paste by mixing with water or other liquid. Hair bleach often contains active ingredients which include an oxidizing agent and an alkaline agent. These agents are often in the form of small particles and have the disadvantage of dusting. The oxidizing and alkaline agents may be harmful if ingested or inhaled; therefore it is desirable to obtain a hair bleach that does not cause this dusting.

Others have apparently attempted to control or reduce the dusting in powdered bleaching compositions. The use of materials such as paraffinic oil and/or waxes is discussed in EP 0,560,088 A1 where the patentees claim they dedust, the bleaching composition by spray application of paraffinic oils and/or waxes. Also, EP 0,583,767 A2 discusses a process for the dedusting of bleaching compositions of specified particle size by the spray application of mineral oil, silicone oil or natural oil. Additionally, U.S. Pat. Nos. 5,622,691 and 5,612,022 state that they achieve dedusting by the application of a water soluble block and/or linear random polyoxyethylene/ polyoxypropylene copolymer. French Patent No. 2,703,588 attempts dedusting by the application of a polypropylene glycol (optionally mixed with a polyalkylene glycol) in a solvent to a bleaching composition of controlled particle size, with the subsequent removal of the solvent.

EP 0,630,643 A1 discusses the spray application of molten polyethylene glycol waxes to bleaching compositions of controlled particle size, followed by subsequent grinding of the composition to eliminate agglomerations caused by the processing. Similarly, EP 0,574,696 A2 discusses a process where two dedusting agents are applied, with the first being a neutralized copolymer of methacrylic acid and methyl methacrylate and the second a water soluble cellulose derivative. None of these references, however, appears to provide a satisfactory dust free hair bleaching composition, nor do they provide a way to minimize the hair damage caused by the actual bleaching process. The methods of making such compositions are usually very process intensive.

SUMMARY OF THE INVENTION

The present invention provides for a composition for bleaching hair comprising: (a) from about 40% to about 70% by weight of a peroxygen compound, and (b) from 0.5% to 15% by weight of a linear hydroxy terminated polyoxypropylene oligomer. The linear hydroxy terminated polyoxypropylene oligomer may comprise, for example, an oil-like material having a pour point less than 0 degress Fahrenheit.

The present invention also provides a process for the preparation of a composition for bleaching hair which comprises mixing a linear hyroxy terminated polyoxypropylene oligomer into a hair bleaching composition, spraying the mixture at room temperature to apply a uniform coating of the oligomer on particles of the hair bleaching composition, thereby causing the particles to agglomerate so as to render the composition essentially dust free during handling.

DETAILED DESCRIPTION OF THE PREFERRED EMBODIMENTS

The bleaching of hair is conventionally accomplished by the application of compositions containing one or more oxidizing agents such as persulfates, percarbonates, peroxides or perborates, an alkali source such as an alkali silicate and various sundry ingredients designed to enhance performance, protect the hair and facilitate the physical handling and application of the bleaching composition. Typically the bleaching composition is mixed with a liquid component commonly known to those familiar with the art as the developer. The developer typically contains hydrogen peroxide and is mixed in varying portions with the bleaching composition to form a viscous liquid or paste-like material which is then applied to the hair to produce the desired bleaching effect.

The bleaching process is decidedly aggressive towards the hair and can result in damage to the hair. The extent of the damage to the hair may be affected by the condition of the hair prior to bleaching, the duration of the bleaching process and/or the bleaching composition itself.

In most cases the bleaching composition is a powder which has fine particles of varying size and is therefore prone to dusting during handling and during any mixing processes. This dust, which may contain various oxidizers, alkalis and other ingredients, is highly irritating to the lungs.

To remedy this persistent problem, the present invention provides an improved composition for bleaching hair comprising: (a) a peroxygen compound, and (b) a linear hydroxy terminated polyoxypropylene oligomer from about 0.5% to about 15% by weight relative to the total weight of the composition. Preferably, the linear hydroxy terminated polyoxypropylene oligomer comprises a water insoluble material having a pour point less than 0 degrees Fahrenheit and has a viscosity between 50 and 2000 centistokes (cSt) at room temperature. The linear hydroxy terminated polyoxypropylene oligomer should preferably have a molecular weight between 300 and 2000 daltons and a single hydroxy terminal group. In a preferred embodiment, the linear hydroxy terminated polyoxypropylene oligomer has a tertiary head group. The head group may be a tertiary butyl. The linear hydroxy terminated polyoxypropylene oligomer preferably will reduce hair damage resulting from a bleaching process.

In one embodiment of the present invention, the peroxygen compound comprises a persulfate, a percarbonate, or a perborate. The composition may be combined with a developer, such as a hydrogen peroxide solution. The developer may be used to make a paste of the bleach to apply it to hair.

The present invention also provides a process for preparing a bleach composition which comprises mixing a linear hydroxy terminated polyoxypropylene oligomer with a powdery oxidizing agent by spraying the linear hydroxy terminated polyoxypropylene oligomer at room temperature, so as to apply an essentially uniform coating of the linear hydroxy terminated polyoxypropylene oligomer to the powdery oxidizing agent, thereby rendering the oxidizing agent essentially dust free. Preferably, the linear hydroxy terminated polyoxypropylene oligomer has a tertiary butyl head group.

Composition

The present invention provides a powdered composition for bleaching hair consisting essentially of at least one oxidizing agent selected from any peroxygen compound and wherein from 0.5% to 15% by weight relative to the total weight of the composition of a linear hydroxy terminated polyoxypropylene oligomer.

The hair bleach composition of the present invention may further comprise: (1) one or more oxidizing agents such as a peroxygen compound, such as a persulfate, a percarbonate, a peroxide or a perborate, (2) an alkali source such as an an alkali earth hydroxide, an alkali earth carbonate, an alkali silicate (e.g., Na silicate, K silicate, a meta silicate, an orthosilicate), a sodium carbonate or a potassium carbonate. The composition may also include other ingredients designed to enhance performance, protect the hair and facilitate the physical handling and application of the bleaching composition.

In another embodiment, the composition may comprise: (1) one or more oxidizing agents and (2) an alkali source.

A developer may be combined with the composition. The developer may comprise a simple hydrogen peroxide solution, which may be from about 3% to about 15% active hydrogen peroxide, and may be in the form of a moderately viscous cream or emulsion containing conditioners and/or emulsifying agents.

Linear Hydroxy Terminated Polyoxypropylene Oligomer

The linear hydroxy terminated polyoxypropylene oligomer used in practicing the present invention is preferably an oil-like substance having a pour point less than 0 degress Fahrenheit, a viscosity between 50 and 2000 centistokes (cSt) at room temperature, and a molecular weight from about 300 to about 12,000 daltons. Preferably, the molecular weight is from about 300 to about 5,000 daltons. More preferably, the molecular weight is from about 300 to about 2,000 daltons. It has a single hydroxy terminal group and is a tertiary butyl initiated polyoxypropylene and is insoluble in water at room temperature.

Advantageously, the linear hydroxy terminated polyoxypropylene oligomer provides enhanced performance in that it functions as a conditioner to the hair and reduces damage to the hair resulting from the bleaching process.

Process

The present invention provides a process for making an improved hair bleach composition wherein the linear hydroxy terminated polyoxypropylene oligomer is introduced into a powdered composition by spraying at room temperature thereby applying a uniform coating of the oligomer on the particles of the composition causing them to agglomerate or stick together and thereby render the composition essentially dust free during handling.

By following the process steps of the present invention, one can produce a powdered bleaching composition having enhanced performance. The composition is dust free during handling and furthermore, the composition is less damaging to hair.

"Less damaging to hair" means that following a bleaching process, the hair is softer to the touch, less dry and has better gloss or shine as compared with equivalent hair being bleached (lightened or highlighted) with a conventional dedusted or non-dusted bleaching composition.

The enhanced performance of the bleaching composition of the present invention is achieved by using a conditioning agent (conditioner) having physical and chemical properties such that it functions as a conditioner, emollient and substantive agent and a dedusting agent.

The specific physical and chemical properties of the linear hydroxy terminated polyoxypropylene oligomer help provide improved results obtainable with the present invention. The chemical structure of the linear hydroxy terminated polyoxypropylene oligomer (conditioner/dedusting agent) is as follows:

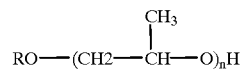

Where n is a whole number from 5 to 200 such that the molecular weight of the conditioner/dedusting agent is from about 300 to about 12,000 daltons. Preferably, the molecular weight is between 300 and 5,000 daltons; and more preferably, the molecular weight is between 300 and 2,000 daltons. The R group can be any alkyl group, preferably a tertiary butyl alcohol. The relatively low molecular weight of the oligomer allows it to remain liquid at temperatures less than 0° F. and to remain sprayable having a viscosity of 50 to 2000 centistokes (cSt). The ability of the material to be sprayed at ambient or below ambient temperatures is an advantage to processing because it allows for the application of the conditioner/dedusting agent without heating. It also minimizes the formation of large agglomerations of particles, which can reduce the free flowing character of the final bleaching composition.

As used herein, the "dedusting agent" or "dedusting conditioner" may be a linear hydroxy terminated polyoxyproplyene oligomer, such as a UCON fluid (available from Union Carbide). For example:

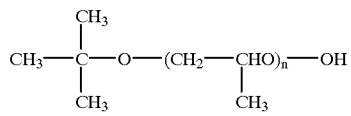

n can be any whole number greater than 0; or

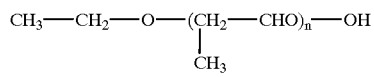

n can be any whole number greater than 0. Preferably, the whole number is between about 5 and about 200 and more preferably is between about 5 and about 50.

The linear hydroxy terminated polyoxypropylene oligomer having a single hydroxyl group is water insoluble at ambient temperatures. The hydrophobic character of the conditioner/dedusting agent enhances the emollient and substantive properties of the material and increases its effectiveness as a dedusting agent.

The present invention also provides for a process for preparing a granular composition useful for bleaching hair, wherein the composition consists essentially of at least one peroxygen compound as an oxidizing agent, and from 0.5% to 15% by weight relative to the total weight of the composition of a linear hydroxy terminated polyoxypropylene oligomer. The ingredients of the composition are processed in such a manner as to produce an essentially dust free, granular composition, with the linear hydroxy terminated polyoxypropylene oligomer also functioning as an emollient and conditioner to the hair and helping to reduce damage to the hair resulting from the bleaching process. The composition is a nearly anhydrous, homogeneous, non-dusting powder.

This invention is illustrated in with actual examples which follow. The examples are set forth to exemplify and aid in an understanding of the invention and are not intended to limit in any way the invention, which is intended to be defined by the claims which are set forth thereafter.

Experimental Details

EXAMPLE 1

A bleaching agent in accordance with this invention having the following composition was prepared:

|  | % by weight |
| --- | --- |
| Ammonium persulfate | 25.0 |
| Potassium persulfate | 20.0 |
| Sodium persulfate | 20.0 |
| Sodium metasilicate | 15.0 |
| Silica | 2.5 |
| Hydrated silica | 2.5 |
| Sodium lauryl sulfate | 2.5 |
| Hydroxyethyl cellulose | 2.5 |
| Conditioner dedusting agent | 10.0 |

The ingredients were added to a blender and blended for fifteen (15) minutes. The conditioner/dedusting agent, UCON® fluid (available from Union Carbide), was then sprayed onto the powder while blending and the entire composition is blended for fifteen (15) additional minutes. The final composition was a granular, free flowing dustless powder. The dedusting agent was sprayed while blending the remaining ingredients at sufficient speed to ensure coverage of all particles and an even dispersal of dedusting agent on the surface of the mixing components.

The bleaching composition was applied to standard light brown hair after mixing with an equal weight of six (6%) aqueous hydrogen peroxide. The hair was processed at 35° C. for twenty five (25) minutes and then rinsed with water, washed with shampoo, rinsed and dried with a hand held hair dryer. A second sample of hair was processed in exactly the same manner using the foregoing bleaching composition, but omitting the conditioner/dedusting agent. Both hair samples were found to have been bleached to the same level. The hair sample processed with the bleaching composition containing the conditioner/dedusting agent had more gloss or shine, was significantly softer to the touch, and was not as dry in appearance as the sample processed in the bleaching composition without the conditioner/dedusting agent.

EXAMPLE 2

|  | % by weight |
| --- | --- |
| Ammonium persulfate | 50.0 |
| Sodium persulfate | 10.0 |
| Sodium metasilicate | 15.0 |
| Silica | 1.0 |
| Hydrated silica | 1.0 |
| Tetrasodium EDTA | 2.5 |
| Hydroxyethyl cellulose | 2.5 |
| Sodium lauryl sulfate | 5.0 |
| Aluminum stearate | 3.0 |
| Conditioner/dedusting agent | 10.0 |

The blending procedure and test procedures for Example 2 were identical to those given for Example 1. The results demonstrate that the composition of Example 2 including the conditioner/dedusting agent of the present invention provides superior results to a bleaching agent lacking the conditioner/dedusting agent.

EXAMPLES 3 & 4

The compositions used in Examples 3 & 4 were identical to Examples 1 and 2, respectively, except that the concentration of the conditioner/dedusting agent was reduced to 5% and the ammonium persulfate was increased by 5%. Test results were also identical.

What is claimed is:

1. A composition for bleaching hair comprising:
   (a) from about 40% to about 70% by weight of a peroxygen compound, and
   (b) about 0.5% to about 15% by weight of a linear hydroxy terminated polyoxypropylene oligomer, wherein the linear hydroxy terminated polyoxypropylene oligomer is water insoluble at ambient temperature.

2. A composition for bleaching hair comprising:
   (a) from about 40% to about 70% by weight of a peroxygen compound, and
   (b) about 0.5% to about 15% by weight of a compound having the formula

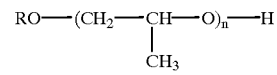

wherein R is a primary, secondary or tertiary alkyl group varying from $C_1$ to $C_{25}$ in length and n is a whole number greater than zero, wherein the compound is water insoluble at ambient temperature.

3. The composition of claim 2, wherein n is a whole number from about 5 to about 200.

4. The composition of claim 2, wherein n is a whole number from about 5 to about 50.

5. The composition of claim 1, wherein the linear hydroxy terminated polyoxypropylene oligomer comprises a water insoluble material having a pour point less than 0 degress Fahrenheit.

6. The composition of claim 1, wherein the linear hydroxy terminated polyoxypropylene oligomer has a viscosity between 50 and 2000 centistokes (cSt) at room temperature.

7. The composition of claim 1, wherein the linear hydroxy terminated polyoxypropylene oligomer has a molecular weight between 300 and 12,000 daltons.

8. The composition of claim 1, wherein the linear hydroxy terminated polyoxypropylene oligomer has a molecular weight between 300 and 5,000 daltons.

9. The composition of claim 1, wherein the linear hydroxy terminated polyoxypropylene oligomer has a molecular weight between 300 and 2,000 daltons.

10. The composition of claim 2, wherein the linear hydroxy terminated polyoxypropylene oligomer has a molecular weight between 300 and 12,000 daltons.

11. The composition of claim 2, wherein the linear hydroxy terminated polyoxypropylene oligomer has a molecular weight between 300 and 5,000 daltons.

12. The composition of claim 2, wherein the linear hydroxy terminated polyoxypropylene oligomer has a molecular weight between 300 and 2,000 daltons.

13. The composition of claim 1, wherein the linear hydroxy terminated polyoxypropylene oligomer has a single hydroxy terminal group.

14. The composition of claim 1, wherein the linear hydroxy terminated polyoxypropylene oligomer contains a tertiary butyl head group.

15. The composition of claim 1, wherein the linear hyroxy terminated polyoxypropylene oligomer is made from an isopropyl alcohol derivative.

16. The composition of claim 1, wherein the peroxygen compound comprises a persulfate, a percarbonate, or a perborate.

17. A process for preparing a dust free hair bleaching composition which comprises:

mixing powdery hair bleach ingredients including from about 40% to about 70% of a peroxygen compound; and spraying a linear hydroxy terminated polyoxypropylene oligomer onto the powdery hair bleaching ingredients at room temperature to coat the powdery hair bleach ingredients, wherein the linear hydroxy terminated polyoxypropylene oligomer is water insoluble at room temperature.

18. The process of claim 17, wherein the linear hydroxy terminated polyoxypropylene oligomer contains a tertiary butyl head group.

* * * * *